United States Patent
Petisce et al.

(10) Patent No.: US 8,834,401 B2
(45) Date of Patent: Sep. 16, 2014

(54) GLUCOSE MANAGEMENT AND DIALYSIS METHOD AND APPARATUS

(71) Applicant: Becton, Dickinson and Company, Franklin Lakes, NJ (US)

(72) Inventors: James R. Petisce, Westford, MA (US); Andrew Metters, Westford, MA (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 103 days.

(21) Appl. No.: 13/685,320

(22) Filed: Nov. 26, 2012

(65) Prior Publication Data

US 2014/0148749 A1  May 29, 2014

(51) Int. Cl.
| | | |
|---|---|---|
| *A61M 37/00* | (2006.01) | |
| *A61M 1/14* | (2006.01) | |
| *A61M 1/36* | (2006.01) | |

(52) U.S. Cl.
CPC .............. *A61M 1/14* (2013.01); *A61M 1/3679* (2013.01); *A61M 1/3621* (2013.01); *A61M 2230/201* (2013.01); *A61M 2202/0486* (2013.01); *A61M 1/3609* (2014.02)
USPC .......................... 604/6.01; 604/5.01; 604/6.06

(58) Field of Classification Search
None
See application file for complete search history.

(56) References Cited

U.S. PATENT DOCUMENTS

| | | |
|---|---|---|
| 5,279,294 A | 1/1994 | Anderson et al. |
| 6,192,891 B1 | 2/2001 | Gravel et al. |
| 7,064,103 B2 | 6/2006 | Pitner et al. |
| 7,629,172 B2 | 12/2009 | Alarcon et al. |
| 8,224,663 B2 | 7/2012 | Gordon |
| 2009/0014340 A1 | 1/2009 | Williams et al. |
| 2010/0298751 A1 | 11/2010 | Schulte et al. |
| 2011/0118578 A1 | 5/2011 | Timmerman |
| 2012/0296253 A1* | 11/2012 | Mathews et al. ............. 604/4.01 |

FOREIGN PATENT DOCUMENTS

| | | |
|---|---|---|
| EP | 1872812 | 1/2008 |
| FR | 2777803 | 10/1999 |

OTHER PUBLICATIONS

Extended European Search Report, dated Jan. 23, 2014, for EP Patent Application No. 13194082.7.

* cited by examiner

*Primary Examiner* — Philip R Wiest
*Assistant Examiner* — Benjamin Klein
(74) *Attorney, Agent, or Firm* — Roylance, Abrams, Berdo & Goodman, L.L.P.

(57) ABSTRACT

A process and apparatus are provided for managing and adjusting glucose levels in the blood of a patient during dialysis. The apparatus is a dialysis apparatus to treat patients with renal disease which includes a glucose scavenger to remove excess glucose from the blood before returning the blood to the patient and/or a device to increase blood glucose levels in the blood when the glucose level is below a threshold level. The glucose scavenger can include a glucose binding protein, boronic acid derivative, boronic ester derivative or mixture thereof bonded to the surface of a support such as a fiber bundle in a cartridge or the inner surface of tubing used in the apparatus.

26 Claims, 2 Drawing Sheets

US 8,834,401 B2

GLUCOSE MANAGEMENT AND DIALYSIS METHOD AND APPARATUS

FIELD OF THE INVENTION

The present invention is directed to a glucose management and dialysis method and apparatus for monitoring a patient's blood glucose concentration during dialysis. In particular, the invention is directed to a glucose management method and apparatus for monitoring blood glucose concentrations during hemodialysis and increasing or decreasing the blood glucose concentration as needed before returning the filtered blood to the patient.

BACKGROUND OF THE INVENTION

Diabetes is an increasing problem today that can lead to numerous disorders. Renal disease and renal failure are some of the more serious consequences of diabetes that is not properly controlled.

Patients who have experienced renal failure require some form of dialysis that is performed several times each week. Hemodialysis is a common form of dialysis that removes the blood from the patient and passes the blood through one or more dialysis filters before returning the blood to the patient. During dialysis, which can take several hours, the patient can experience a lowering of the blood glucose level. The patient often experiences a loss of appetite after dialysis so that the patient does not eat immediately after the completion of the dialysis treatment. This can result in lowering of the blood glucose level in the patient. Patients sometimes eat before beginning dialysis treatment since they can experience a loss of appetite after treatment. This can result in spikes in the blood glucose level at the beginning of the dialysis treatment.

Glucose levels are typically monitored at period intervals by the patient to determine when an insulin injection may be necessary or to determine how the user is responding to the prior injections. The patient monitors the blood glucose levels by lancing a portion of the body with a lancet to take a blood sample. The blood sample is placed on a test strip that contains appropriate enzymatic reagents for measuring blood glucose levels, which is subsequently analyzed by a blood glucose monitor. Various devices are known that are able to monitor blood glucose levels to assist a diabetic in the proper treatment. Examples of such devices are disclosed in U.S. Pat. No. 8,224,663 to Gordon, U.S. Pat. No. 5,279,294 to Anderson et al. and U.S. Pat. No. 6,192,891 to Gravel et al.

Biosensors have also been developed for measuring and monitoring blood glucose levels. These devices typically use a glucose binding protein that is able to capture glucose and produce a detectable signal for measuring the blood glucose level in the patient. Examples of glucose binding proteins used in biosensors are disclosed in U.S. Pat. No. 7,629,172 to Alarcon et al. and U.S. Pat. No. 7,064,103 to Pitner et al. which are hereby incorporated by reference in their entirety.

While the prior devices have been suitable for their intended purposes, there is a continuing need in the industry for a system that is able to monitor and adjust blood glucose levels in a patient at times when the patient is not able to take the sample by the finger stick methods that are commonly used today.

SUMMARY OF THE INVENTION

The invention is directed to a dialysis method for treating a patient and monitoring the blood glucose concentration during dialysis. The invention is also directed to a hemodialysis method and apparatus for adjusting the blood glucose concentration of blood during the dialysis process before returning the filtered and treated blood to the patient.

The invention is particularly directed to a glucose management method and apparatus for use during dialysis or during other procedures where blood is removed from a patient, treated and returned to the patient, such as oxygenation during surgery. Accordingly, one object of the invention is to provide a method and apparatus that is able to perform dialysis for a patient while monitoring the blood glucose level of the patient at predetermined time intervals or continuously, and adjusting the patient's blood glucose level to a predetermined range.

Another feature of the invention is to provide a method and apparatus that is able to increase or decrease a patient's blood glucose concentration during hemodialysis before returning the treated blood to the patient. A further feature of the invention is to provide a method and apparatus for scavenging glucose from blood of a patient to lower the blood glucose concentration to within a predetermined range using a glucose binding protein.

One aspect of the invention is to provide a dialysis apparatus with a glucose monitoring unit that can monitor blood glucose concentrations continuously or at predetermined intervals or cycles. The glucose monitoring unit can be programmed to direct the patient's blood after the dialysis and filtering treatment to a device for increasing the blood glucose concentration before returning the blood to the patient, to a device for reducing the blood glucose level before returning the blood to the patient, or for returning the blood to the patient without further treatment, based on the measured blood glucose level.

Another feature of the invention is to provide a dialysis apparatus having a glucose monitoring device that produces a visual or audible signal to a technician when the blood glucose level falls outside a predetermined range. The technician can then direct the flow of blood to a device to increase or decrease the glucose concentration before returning the blood to the patient.

Another feature of the invention is to provide a device for reducing the blood glucose concentration in blood where the device includes a glucose binding protein, a boronic acid, boronic ester or mixture thereof fixed to a support. The device can be a cartridge that can be connected to the flow path of a dialysis apparatus. The cartridge can be connected to the inlet side or outlet side of the dialyser.

A further feature of the invention is to provide a device for increasing the blood glucose concentration of blood after dialysis and before returning the blood to the patient. The device can include a supply for introducing dextrose or glucose into the blood, introducing a pharmaceutical agent for inducing glucose production in the patient, or a glucose binding protein on a support in a glucose solution having a concentration to introduce the glucose into the blood.

The various aspects of the invention are basically obtained by providing a hemodialysis process for treating a patient such as a dialysis patient. The process comprises removing blood from the patient, passing the blood through a treatment device, such as a dialyser to treat and filter the blood, and measuring the glucose level of the blood removed from the patient. The blood is directed to a glucose scavenging unit containing a glucose binding protein, boronic acid, boronic ester or mixture thereof when the glucose level is measured above a threshold level and glucose is removed from the blood. A reduced glucose level blood is produced, and the reduced glucose level blood is returned to the patient.

The features of the invention are further obtained by providing a dialysis process which comprises introducing a dialysis fluid into a patient and removing blood from the patient to a dialyser to remove wastes from the blood. Glucose levels in the blood are monitored and glucose levels above a predetermined threshold are detected. The blood is directed to a glucose scavenger when the blood glucose level of the blood is above the threshold level. The glucose is removed from the blood or to a unit for increasing a blood glucose level when the blood glucose level is below the predetermined threshold level, and the blood is thereafter returned to the patient.

The features of the invention are also obtained by providing a dialysis apparatus which comprises a first supply line for removing blood from a patient, a dialyser unit coupled to the first supply line for receiving the blood from the patient, and for treating the blood by removing waste from the blood. A glucose monitoring unit receives the blood for measuring a glucose level in the blood, detecting a blood glucose level in the blood above a threshold level, and detecting a blood glucose level in the blood below a threshold level. A glucose scavenger unit having a glucose binding protein, boronic acid, boronic ester or mixture thereof is adapted for receiving the blood and removing a predetermined amount of glucose from the blood when the glucose level is above the threshold level. A second supply line returns treated blood from the dialyser to the patient.

These and other objects, advantages and features of the invention will become apparent from the following detailed description of the invention, which in conjunction with the drawings, disclose various embodiments of the invention.

BRIEF DESCRIPTION OF THE DRAWINGS

The following is a brief description of the drawings, in which.

DETAILED DESCRIPTION OF THE INVENTION

Figure 1:
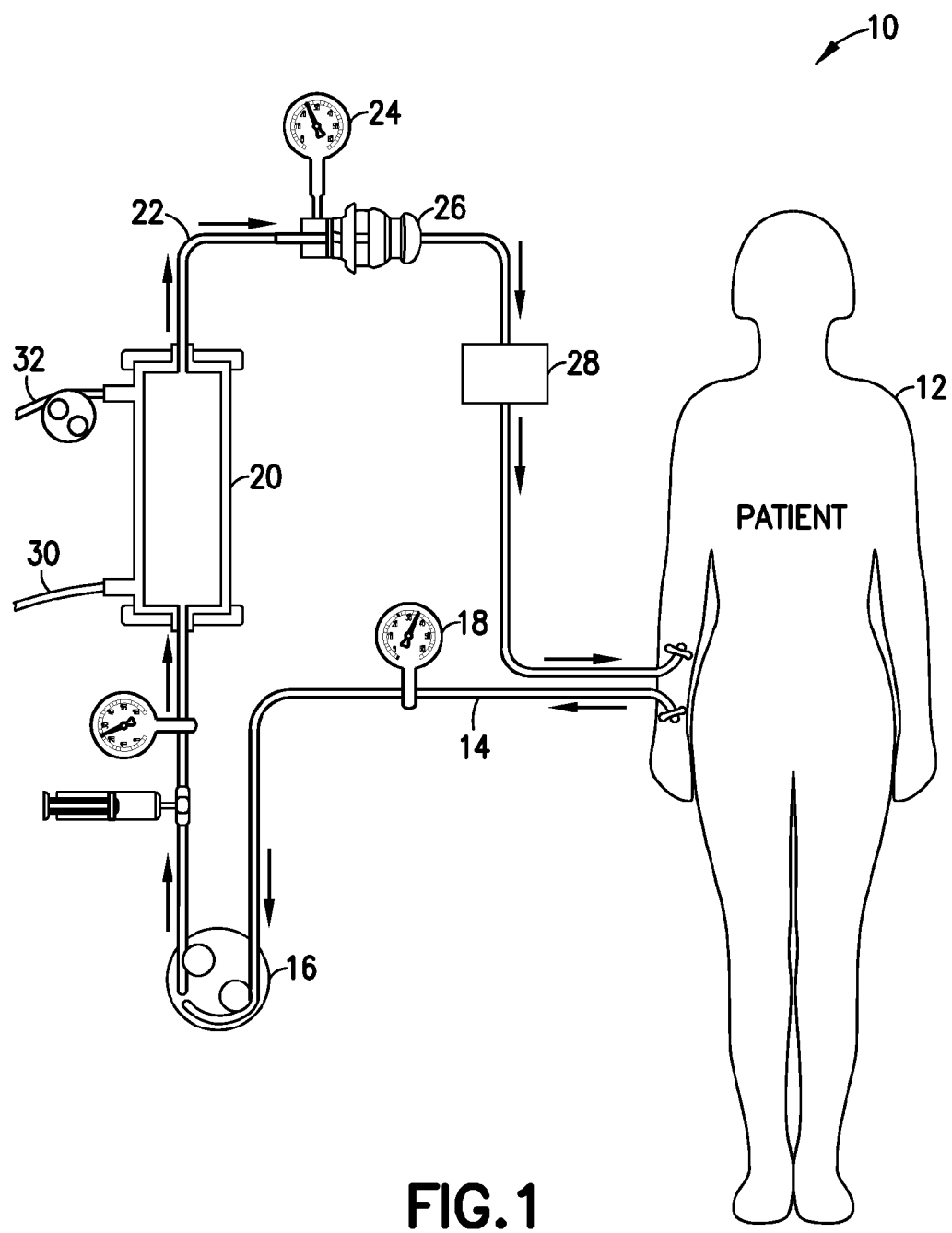
FIG. 1 is a schematic diagram of a dialysis system having a glucose management device.

Referring to FIG. 1, a hemodialysis system 10 according to one embodiment of the invention is shown. Dialysis system 10 removes blood from a patient 12 by a tube 14 using a pump 16. In the embodiment shown, a pressure monitor 18 is provided in line with tube 14. Pump 16 conveys the blood from patient 12 to a dialyser 20 where the blood is treated and filtered to remove wastes from the blood. The filtered blood exits dialyser 20 through a tube 22 which can be connected to a pressure monitor 24 and an air trap 26. The treated blood is then passed through a glucose monitoring and adjusting assembly 28 to increase or decrease the blood glucose level as needed before returning the blood to the patient 12.

Dialyser 20 in one embodiment of the invention is a standard dialyser unit as known in the art. Typically, dialyser 20 passes the patient's blood through a partially permeable membrane. Dialyser 20 can include a plurality of small synthetic hollow fibers that act as a semi-permeable membrane. Blood flows through the hollow fibers and a dialysis solution flows around the fibers from a supply line 30 where water and wastes move through the semi-permeable membrane defined by the wall of the hollow fibers between the dialysis solution and the blood. The spent dialysis solution is removed from dialyser 20 through a discharge line 32. Ultrafiltration occurs by increasing the hydrostatic pressure across the semi-permeable membrane in dialyser 20. This is typically carried out by applying a negative pressure to a dialysate compartment of dialyser 20. The pressure gradient causes water and dissolved waste solutes to move from the blood to the dialysis solution.

Figure 2:
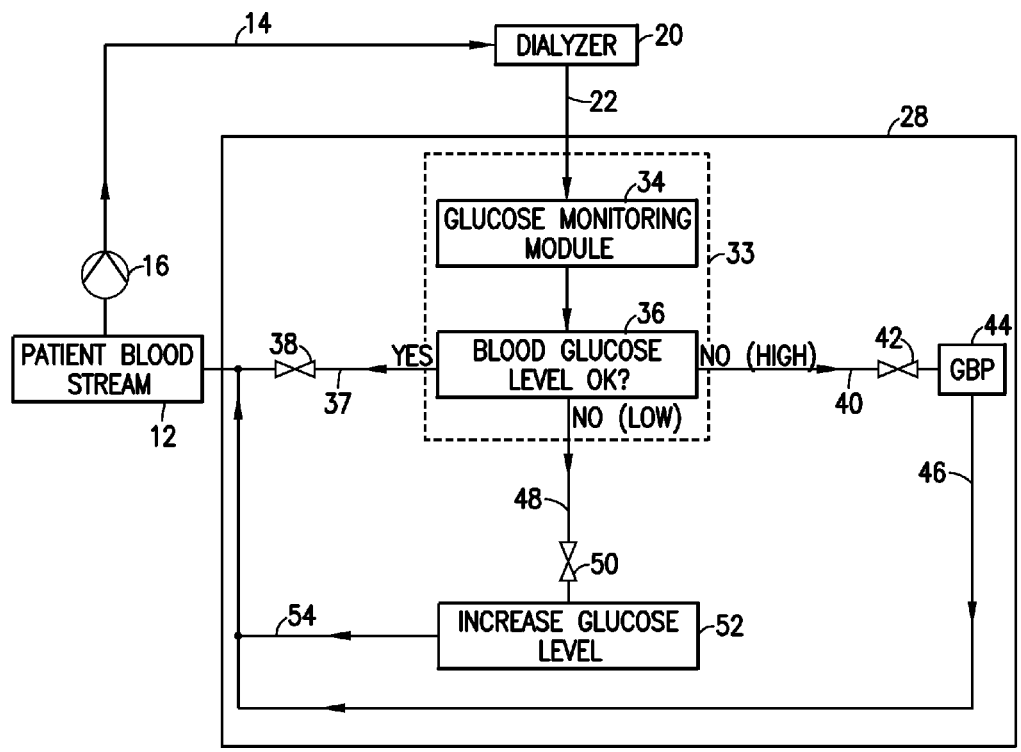
FIG. 2 is a schematic diagram of the dialysis system showing the flow paths of the glucose management device.

FIG. 2 is a schematic diagram showing the details of dialysis system 10 and depicting a flow diagram of glucose monitoring and adjusting assembly 28 through the components of the system. In the embodiment illustrated, a glucose monitoring assembly 33 is positioned downstream of dialyser 20 in output line 22. Glucose monitoring assembly 33 includes a glucose monitoring module 34 for measuring the glucose level in blood after dialysis and before being returned to patient 12 and a control unit 36 for directing the blood to the selected treatment module. Glucose monitoring module 34 can measure the glucose level at selected time intervals or at a selected frequency. Glucose monitoring module 34 can be based on conventional finger stick meter technology as known in the art that is able to determine the blood glucose level and provide a display that is visible or audible by a technician.

In other embodiments, glucose monitoring module 34 can be a continuous glucose monitor that is able to produce a signal indicating a high glucose level or a low glucose level in the blood. The high and low glucose level thresholds can be predetermined values or selected by a technician for each individual patient. The high glucose signal and the low glucose signal can actuate a visible or audible alarm to prompt the technician to divert all or a portion of the blood to a suitable treatment site. In an alternative embodiment, the assembly 28 can be connected to a side loop in the output line 22 of dialysis system 10 and controlled by valves to divert all or a portion of the blood through the assembly as needed.

As shown in FIG. 2, the blood glucose level is monitored by glucose monitoring module 34 of assembly 28 and compared with predetermined known values by a control unit indicated by block 36 to determine whether the blood glucose level is high, low, or falls within an acceptable range. When the blood glucose level as measured falls within an acceptable range, the blood is returned unchanged to patient 12 through line 37. A valve 38 is provided in line 37 to allow blood to pass through line 37 to patient 12 when the blood glucose level is within an acceptable range. Valve 38 can be controlled automatically by glucose monitoring module 34 and control unit 36 based on the measured blood glucose level so that the blood is automatically returned to the patient without further treatment.

In the event the blood glucose level as determined by glucose monitoring module 34 is above a predetermined threshold level or above an acceptable range, blood is diverted by control unit 36 through line 40 by a valve 42 to a unit 44 for reducing the blood glucose level in the blood. In one preferred embodiment, unit 44 contains a glucose binding protein to scavenge or capture glucose to reduce the blood glucose level to an acceptable range before returning the blood to the patient through line 46.

When the blood glucose level as measured by glucose monitoring unit 34 is below a predetermined level or below an acceptable range, blood is diverted by control unit 36 through line 48 and valve 50 to a glucose increasing module or unit 52 for increasing the blood glucose level to an acceptable level. The blood is then directed through line 54 where it is returned to patient 12. The glucose increasing unit 52 can be a removable or replaceable cartridge that is adapted for introducing a substance into the blood to increase the blood glucose level to a predetermined range. In one embodiment, unit 52 introduces a source of glucose or dextrose to the blood. The source of glucose can be a 50% aqueous solution of dextrose (D50) or a pharmaceutical agent, such as glucagon, for inducing the patient's liver to release glucose to the bloodstream. The source of glucose can also be a container or cartridge having a support with a glucose binding protein, boronic acid, boronic ester and derivatives thereof or other reversible glucose binding agent that is able to release glucose to the blood stream under controlled conditions.

In one embodiment of the invention, glucose monitoring module 34 automatically opens and/or closes each of valves 38, 42 and 50 based on the measurement of the blood glucose level to divert the flow of blood to the appropriate treatment unit. Each of the valves can be controlled by a suitable control mechanism such as control unit 36 including a microprocessor that is able to open and close the valves based on the blood glucose level after dialysis. In an alternative embodiment, glucose monitoring module 34 or control unit 36 includes a display that is able to display the measured blood glucose level for the technician. The technician can then manually operate the appropriate valves to direct the blood to the selected path for treatment. The glucose monitoring module can produce a visual or audible alarm to alert the technician to an abnormal glucose level.

In one preferred embodiment, the glucose adjusting assembly 28 is provided downstream of dialyser 20 so that the blood glucose level can be reduced or increased as needed just prior to returning to patient 12 and after filtering in dialyser 20, since the dialyser may remove glucose or other components from the blood that may avoid the need for further treatment of the blood. It is generally preferred to adjust the blood glucose level as necessary after dialysis to avoid the dialysis step from removing glucose during the filtration step. A second glucose monitoring unit in another embodiment can be included downstream of the treatment sites to record the blood glucose level being returned to the patient.

In one preferred embodiment, glucose reducing unit 44 is a replaceable cartridge having an inlet and an outlet connected to line 40 to receive blood when the measured blood glucose level is above a predetermined threshold level. The cartridge contains a scavenger such as a glucose binding protein (GBP), boronic acid, boronic ester, derivatives and mixtures thereof attached to the support for scavenging glucose from the blood to reduce the blood glucose level to an acceptable level. The amount of glucose scavenged from the blood by the GBP, boronic acid or boronic ester can be selectively tailored by adjusting the glucose binding constant (Kd) of the GBP, boronic acid or boronic ester so that only a selected and controlled amount of glucose is removed from the blood.

The support for the glucose scavenger such as GBP is preferably a suitable material capable of forming a covalent bond with glucose scavenger to fix the glucose scavenger to the support and prevent the GBP from entering the bloodstream of the patient. The support can be in the form of fibers, membranes, films and solid particles. A coupling agent such as 1-ethyl-3-(3-dimethyl-aminopropyl)carbodiimide (EDC) is used to bind the GBP to the support surface. Other methods for fixing the GBP to a solid support can be used as known in the art. For example, GBP is known for use in biosensors to monitor blood glucose levels where the GBP is fixed to a support surface. The support surface is made from a suitable polymer or coating on the substrate having a reactive binding site capable of reacting with EDC. EDC is a water soluble carbodiimide using a carboxyl activating agent for the coupling of primary amines to yield amide bonds.

Figure 3:
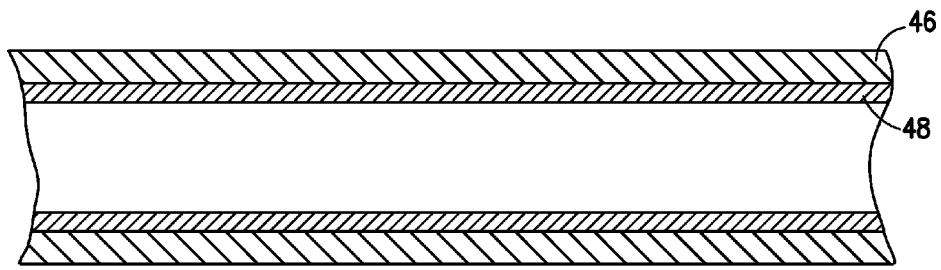
FIG. 3 is a cross-sectional view of a glucose scavenging unit in an embodiment of the invention.

The solid support can be made of polymer produced by Saint-Gobain Corporation under the trademark TYGON. TYGON can be produced in the form of fibers, membranes, films and particles which can fix a GBP to the surface thereof using a coupling agent such as EDC. In another embodiment shown in FIG. 3, the glucose reducing unit is a length of flexible tubing 46 having an inner surface with a GBP 48 covalently bonded thereto. The tubing 46 can be made of TYGON, although other materials can be used. Suitable plastic materials are preferably clear, easily sterilized, do not contain any leachable components, have sufficient strength and flexibility during use under pressure while pumping and are capable of binding with a coupling agent for attaching a GBP to the tubing. The amount of the GBP fixed to the tubing and the length of the tubing are selected to remove a controlled amount of glucose from the blood before returning the blood to the patient. Preferably, the tubing is a supply line positioned downstream of the dialyser and the glucose monitoring module and immediately before returning the blood to the patient. The amount of glucose removed from the blood can be controlled by the length of the tubing or the surface area of the GBP or other glucose scavenging agent. In other embodiments, the length of tubing can be a supply line for directing blood from the patient to the dialyser.

The GBP can be any suitable protein capable of binding to glucose and scavenging glucose from blood at a sufficient rate and amount during dialysis of a patient. Examples of glucose binding proteins are disclosed in commonly owned U.S. Pat. Nos. 6,855,556, 7,064,103 and 7,629,172, which are hereby incorporated by reference in their entirety.

The Galactose/Glucose Binding Protein, referred to as "GBP" or "GGBP" as used herein refers to a type of protein naturally found in the periplasmic compartment of bacteria. These proteins are naturally involved in chemotaxis and transport of small molecules (e.g., sugars, amino acids, and small peptides) into the cytoplasm. GGBP is a single chain protein consisting of two globular $\alpha/\beta$ domains that are connected by three strands to form a hinge. The binding site is located in the cleft between the two domains. When glucose enters the binding site, GGBP undergoes a conformational change, centered at the hinge, which brings the two domains together and entraps glucose in the binding site. X-ray crystallographic structures have been determined for the closed form of GGBP from *E. coli*.

Mutated Binding Protein (for example "mutated GGBP") refers to binding proteins from bacteria containing an amino acid(s) which has been substituted for, deleted from, or added to the amino acid(s) present in naturally occurring protein.

Exemplary mutations of binding proteins include the addition or substitution of cysteine groups, non-naturally occurring amino acids (Turcatti, et al. J. Bio. Chem. 1996 271, 33, 19991-19998, incorporated by reference herein) and replacement of substantially non-reactive amino acids with reactive amino acids to provide for the covalent attachment of electrochemical or photo-responsive reporter groups.

Exemplary mutations of the GGBP protein include a cysteine substituted for a lysine at position 11 (K11C), a cysteine substituted for aspartic acid at position 14 (D14C), a cysteine substituted for valine at position 19 (V19C), a cysteine substituted for asparagine at position 43 (N43C), a cysteine substituted for a glycine at position 74 (G74C), a cysteine substituted for a tyrosine at position 107 (Y107C), a cysteine substituted for threonine at position 110 (T110C), a cysteine substituted for serine at position 112 (S112C), a double mutant including a cysteine substituted for a serine at position 112 and serine substituted for an leucine at position 238 (S112C/L238S), a cysteine substituted for a lysine at position 113 (K113C), a cysteine substituted for a lysine at position 137 (K137C), a cysteine substituted for glutamic acid at position 149 (E149C), a double mutant including a cysteine substituted for an glutamic acid at position 149 and a serine substituted for leucine at position 238 (E149C/L238S), a double mutant comprising a cysteine substituted for histidine at position 152 and a cysteine substituted for methionine at position 182 (H152C/M182C), a double mutant including a serine substituted for an alanine at position 213 and a cysteine substituted for a histidine at position 152 (H152C/A213S), a cysteine substituted for an methionine at position 182 (M182C), a cysteine substituted for an alanine at position 213 (A213C), a double mutant including a cysteine substituted for an alanine at position 213 and a cysteine substituted for an leucine at position 238 (A213C/L238C), a cysteine substituted for an methionine at position 216 (M216C), a cysteine substituted for aspartic acid at position 236 (D236C), a cysteine substituted for an leucine at position 238 (L238C) a cysteine substituted for a aspartic acid at position 287 (D287C), a cysteine substituted for an arginine at position 292 (R292C), a cysteine substituted for a valine at position 296 (V296C), a triple mutant including a cysteine substituted for an glutamic acid at position 149 and a alanine substituted for a serine at position 213 and a serine substituted for leucine at position 238 (E149C/A213S/L238S), a triple mutant including a cysteine substituted for an glutamic acid at position 149 and a alanine substituted for an arginine at position 213 and a serine substituted for leucine at position 238 (E149C/A213R/L238S).

In the event glucose monitoring module 34 detects a low blood glucose level or hypoglycemic condition, valve 48 is opened to direct blood to glucose increasing module 52. Typically, valves 38 and 42 are closed to direct all of the blood through module 52. Glucose increasing module 52 is provided to increase the blood glucose level in the blood before returning the blood to patient 12. A low blood glucose level can be treated by the addition to the blood of a component such as glucagon, dextrose such as D50, or a pharmaceutical agent capable of inducing the patient to produce glucose or increase glucose levels. In an alternative embodiment, the blood can be passed through a cartridge containing GBP on a support charged with a predetermined amount of glucose to release at least a portion of the glucose to the blood. The glucose binding protein fixed to a support surface is typically in a glucose solution in equilibrium with the blood under normal conditions. By increasing the amount or concentration of glucose in the solution, a portion of the glucose can diffuse into the blood to increase the blood glucose levels as needed.

In another embodiment the glucose scavenger or glucose-binding agent is a boronic acid or boronic ester derivative that is able to reversibly bind to glucose in the blood for scavenging glucose from the blood. As in THE embodiment previously discussed, the blood can be directed through a glucose scavenging unit when the blood glucose level is above a predetermined level to reduce the blood glucose level. The boronic acid and/or boronic ester are also suitable eluting glucose when the blood glucose level is below a predetermined level. The boronic acid and boronic ester derivatives can have the formula

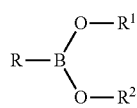

where R is an organic group, $R^1$ and R2 are independently H, an organic group, or $R^1$ and $R^2$ can together be —$R^3$—. The R, $R^1$, $R^2$ and $R^3$ groups are selected to enable binding with glucose or other target molecules. Suitable boronic acids include phenyl boronic acid, napthyl boronic acid and anthreacene boronic acid.

R can be a substituted or unsubstituted alkyl, a substituted or unsubstituted alkylene, heterocyclic, or an aryl group. In one embodiment R is a lower alkyl such as a methyl, ethyl or propyl group or a lower alkylene group such as a propylenyl group. In other embodiments R can be an aryl group selected from the group consisting of phenyl, substituted phenyl, anthracene, substituted anthracenes, naphthalene and substituted naphthalenes. An example of a heterocylic group is a thiophene group. R can be other suitable organic groups that contain a suitable marker.

In further embodiments, R can be an N substituted or amine based boronic acid. Amine based boronic acids are particularly suitable for fluorescent boronic acid sensors where the boronic acid includes a fluorophore. Fluorescent groups benefit from having an amine group proximal to the boron. The Lewis acid-Lewis base interaction between the boronic acid and the tertiary amine enables molecular recognition to occur at neutral pH and is able to indicate binding by modulating the intensity of fluorescence. Examples of suitable boronic acid derivatives are disclosed in U.S. Pat. No. 5,503,770 to James et al., U.S. Pat. No. 5,763,238 to James et al., U.S. Pat. No. 7,829,341 to Gamey et al. and U.S. Pat. No. 8,178,676 to Gamey et al. which are hereby incorporated by reference in their entirety.

$R^1$ and $R^2$ are typically H or a lower alkyl selected from the group consisting of methyl, ethyl or propyl. $R^3$ can be ethylene, propylene or 3-methoxy propylene.

Boronic acid and boronic esters are known to have a reversible binding affinity with 1,2 and 1,3 diols. The hydroxyl groups of the diols react with the boronic acid group in an aqueous medium to form 5 or 6-membered cyclic esters. The reaction is reversible to release the diol by adjusting the conditions of the aqueous medium. Boronic acids and esters thereof are known to have a reversible binding affinity for saccharides.

The boronic acid and boronic esters can be attached or bonded to a support in the form of a membrane, film, strands or other shape. Typically the R group contains a suitable reactive group that can bind with a reactive site on the support. The support can be formed into a replaceable cartridge that can be positioned in the flow path of the blood before or after dialysis. The support can be a thin polymer layer having the boronic acid bonded to and immobilized thereon. Suitable polymers are hydrophilic and can include polymers such as cross-linked polyurethanes, polyacrylanides, poly(hydroxyethyl methacrylates)polyalcohols and selected polysaccharides.

The boronic acid and boronic esters are able to be selective to scavenge glucose from the blood by passing the blood through a membrane containing the boronic acid or boronic esters. The glucose scavengers can be modified to enable only predetermined amounts of the glucose to be removed from the blood. In other embodiments the boronic acid and boronic esters can be loaded with glucose to elute glucose into the blood when the blood glucose level of the blood is below a predetermined lever.

In one embodiment of the invention, glucose monitoring module 34 monitors the blood glucose level of the blood continuously or at selected time intervals throughout the dialysis of the patient. The glucose monitoring unit continuously directs the blood through the appropriate path based on the measured glucose level in the blood. For example, where the blood glucose level as measured is euglycemic and falls within an acceptable predetermined range, valve 38 is opened to return the blood directly to the patient while closing valves 42 and 48. When a hyperglycemic valve 42 is opened, the blood is directed through the glucose binding protein cartridge to scavenge at least a portion of the glucose from the blood.

The glucose monitoring unit 34, in one embodiment, can direct all or only a portion of the blood through the glucose scavenging unit to remove an amount of glucose from the blood to achieve a predetermined level. Once a patient's blood glucose concentration becomes euglycemic, valve 42 is closed and valve 38 is opened. In a similar manner, when glucose monitoring unit 34 measures a hypoglycemic condition, valve 48 is opened and valve 38 is closed to direct the blood through unit 52 to increase the blood glucose level until a euglycemic condition is detected. At that time, valve 48 can be closed and valve 38 can be opened to return the blood to the patient.

The glucose increasing unit includes a glucose host material, such as a glucose binding protein, boronic acid or boronic acid ester that is capable of reversibly binding glucose. The binding ability of a glucose host material is referred to as its dissociation constant (Kd). As the Kd increases, the host material binds glucose less strongly resulting in a higher ratio of unbound glucose to bound glucose. In the present invention wherein a host material or host material system is charged with glucose to act of a source of glucose for a blood flow sample having a less than desired glucose concentration, the ability of the host material charged with glucose to increase the glucose concentration in the blood flow sample is optimized by appropriate adjustment of the Kd of the host material/glucose complex.

Since blood glucose levels less than about 80 mg/dL can cause a hypoglycemic response in humans, the Kd of the host material/glucose complex could be adjusted to release glucose into a blood sample having a glucose concentration below this amount, for example.

The host material can be deposited onto a support, such as the inner walls of flexible tubing contained within a blood flow of a device which pumps blood from a person for a variety of purposes including, for example, hemodialysis. Alternatively, the host material can be deposited into the membranes of a cartridge which contains such membranes. Optimally, the host material is covalently bonded to a support surface whether it be a flexible tubing inner surface or a membrane within a cartridge. Prior to actual use, the host material is charged with glucose by flowing a glucose containing solution over the support surface.

The support surface can minimally contain only one glucose host. Alternatively, the support surface can contain more than one glucose host. The glucose host can be a glucose binding protein (GBP), a boronic acid (BA) or a boronic acid ester (BE), or mixtures thereof. The loading of the support surface is optimized to deliver a targeted amount of glucose into a bloodstream flowing over or through the support.

In one embodiment, more than one membrane containing cartridges in which the glucose host charged with glucose has been covalently bound is connected to an automatic valve that is system activated when a low threshold glucose concentration is detected by an inline continuous glucose monitor. Should the continuous glucose monitor continue to read an unacceptably low glucose value after a predetermined time period, blood flow is diverted through the automatic valve system to a second such cartridge system.

In another embodiment, an analogous system to the previous embodiment exists in which the cartridge or series of cartridges are replaced with a series of flexible tubing loops having inner surfaces supporting a covalent bound glucose host which has been charged with glucose before use.

In either embodiment, when the continuous glucose monitor detects a glucose concentration above a designated low threshold level, blood is no longer flowed through the glucose increasing cartridge or tubing by actuation of an automatic valving system.

The embodiment of the invention disclosed herein relates to monitoring and adjusting blood glucose levels in a dialysis patient. In other embodiments, the glucose management system of monitoring and adjusting glucose blood levels in other procedures where blood is removed from a patient, treated in a suitable manner and returned to the patient. For example, the glucose management system can be used in combination with a heart-lung machine that is primarily used to oxygenate blood during surgery so that the blood glucose levels can be monitored and adjusted as necessary.

While various embodiments have been described herein, it will be understood by one skilled in the art that various changes and modifications can be made without departing from the scope of the invention as defined in the appended claims and their equivalents.

What is claimed is:

1. A process for treating a patient, the process comprising:
    removing blood from the patient and passing the blood through a treatment device to treat the blood, where said treatment device is a dialyser to treat the blood by removing wastes from the blood;
    measuring the glucose level of the blood;
    directing the blood to a glucose scavenging unit when the measured glucose level is measured above a threshold level and removing glucose from the blood, and producing a reduced glucose level blood, or directing the blood to a glucose increasing unit when the measured glucose is below a threshold level and increasing the blood glucose level, where said glucose scavenging unit is positioned in a line between the dialyser and the patient; and
    returning the resulting treated blood to said patient.

2. The process of claim 1, wherein said method further comprises
    passing said blood through said glucose scavenging unit before passing through said dialyser.

3. The process of claim 1, wherein
    said glucose scavenging unit includes a glucose scavenger selected from the group consisting of a glucose binding protein, a boronic acid and a boronic ester and mixtures thereof on a support and where the glucose scavenger has a predetermined glucose binding constant Kd.

4. The process of claim 3, where said boronic acid is selected from the group consisting of phenyl boronic acid, naphthyl boronic acid and anthracenyl boronic acid.

5. The process of claim 3, wherein
    said support comprises a porous membrane.

6. The process of claim 3, wherein
    said scavenging unit comprises a length of flexible tubing having an inner surface with the glucose binding protein bonded thereto.

7. The process of claim 6, wherein
    said glucose binding protein, boronic acid or boronic ester is covalently bonded to the inner surface of said tubing.

8. The process of claim 1, further comprising
    introducing glucose or D50 into the blood in the glucose increasing unit to increase the blood glucose level to a predetermined range.

9. The process of claim 1, further comprising
    introducing glucagon to the blood in the glucose increasing unit to promote glucose production in the patient.

10. A dialysis process comprising:

removing blood from a patient to a dialyser to remove waste from the blood;

monitoring blood glucose levels in the blood and detecting glucose levels above a predetermined threshold and/or below a predetermined threshold;

directing the blood to one of a glucose scavenger when the blood glucose level of the blood is above said threshold level and removing the glucose from said blood, or to a glucose increasing unit for increasing a blood glucose level when the blood glucose level is below said predetermined threshold level and increasing the blood glucose level, where said glucose scavenging unit is positioned in a line between the dialyser and the patient; and thereafter returning said blood to said patient.

11. The process of claim 10, further comprising passing the blood through the glucose scavenger before passing through the dialyser.

12. The process of claim 10, further comprising passing the blood through the glucose scavenger after passing through the dialyser.

13. The process of claim 10, wherein said glucose scavenger comprises a cartridge connected to the dialyzer and where said glucose scavenger is selected from the group consisting of glucose binding proteins, boronic acids, boronic esters and mixtures thereof fixed to a support.

14. The process of claim 13, wherein said glucose scavenger is a glucose binding protein having a predetermined glucose binding constant Kd.

15. The process of claim 10, wherein said glucose scavenger comprises a conduit having an inner wall with the glucose binding protein, boronic acid or boronic ester covalently bonded thereto and said process further comprises passing said blood through said conduit before returning said blood to said patient.

16. The process of claim 10, further comprising introducing glucose or D50 to the blood in the glucose increasing unit when the measured blood glucose level is below the predetermined threshold level.

17. The process of claim 10, further comprising introducing glucagon into the blood in the glucose increasing unit when the measured blood glucose level is below the predetermined threshold level to promote glucose production in the patient.

18. A dialysis apparatus comprising:

a first supply line for removing blood from a patient;

a dialyser unit coupled to said first supply line for receiving the blood from the patient, and for treating the blood by removing waste from said blood;

a glucose monitoring unit receiving the blood for measuring a glucose level in the blood, detecting a blood glucose level in the blood above a threshold level and detecting a blood glucose level in the blood below a threshold level;

a glucose scavenging unit having a glucose scavenger selected from the group consisting of glucose binding proteins, boronic acids, boronic esters and mixtures thereof, said glucose scavenger adapted for receiving the blood and removing a predetermined amount of glucose from the blood when the glucose level is above said threshold level; and a second supply line for returning treated blood from said dialyser to the patient.

19. The dialysis apparatus of claim 18, wherein said glucose scavenging unit comprises a cartridge and is positioned upstream of said dialyser unit.

20. The dialysis apparatus of claim 18, wherein said glucose scavenging unit comprises a cartridge and is positioned downstream of said dialyser unit.

21. The dialysis apparatus of claim 18, further comprising a control unit for diverting blood to said glucose scavenging unit when the detected glucose level in the blood is above the threshold level.

22. The dialysis apparatus of claim 18, wherein said first supply line or second supply line comprises a tube having an inner surface with the glucose scavenger covalently bonded thereto for scavenging a predetermined amount of glucose from said blood.

23. The dialysis apparatus of claim 18, further comprising a glucose increasing unit positioned downstream of said dialyser for increasing blood glucose levels in said blood, and where said control unit directs said blood from said dialyser to said device when the measured blood glucose level is below a threshold level.

24. The dialysis apparatus of claim 23, wherein said glucose increasing unit introduces glucose or D50 into the blood to increase the blood glucose level to a predetermined level.

25. The dialysis apparatus of claim 23, wherein said glucose increasing unit introduces glucagon into the blood to promote glucose production in the patient.

26. The dialysis apparatus of claim 23, wherein said glucose increasing unit includes a glucose binding protein, a boronic acid or boronic ester charged with glucose for releasing glucose to the blood.

* * * * *